US009040704B2

(12) United States Patent
Piers et al.

(10) Patent No.: US 9,040,704 B2
(45) Date of Patent: May 26, 2015

(54) FLUORESCENT DYES WITH LARGE STOKES SHIFTS

(75) Inventors: Warren Edward Piers, Calgary (CA); Juan Felipe Araneda, Calgary (CA)

(73) Assignee: UTI LIMITED PARTNERSHIP, Calgary, Alberta (CA)

( * ) Notice: Subject to any disclaimer, the term of this patent is extended or adjusted under 35 U.S.C. 154(b) by 0 days.

(21) Appl. No.: 14/238,640

(22) PCT Filed: Aug. 10, 2012

(86) PCT No.: PCT/CA2012/050544
§ 371 (c)(1),
(2), (4) Date: Mar. 26, 2014

(87) PCT Pub. No.: WO2013/023292
PCT Pub. Date: Feb. 21, 2013

(65) Prior Publication Data
US 2014/0206870 A1    Jul. 24, 2014

Related U.S. Application Data

(60) Provisional application No. 61/522,829, filed on Aug. 12, 2011.

(51) Int. Cl.
*C09B 23/16*    (2006.01)
*C09K 11/06*    (2006.01)
*G01N 33/58*    (2006.01)

(52) U.S. Cl.
CPC ............ *C09B 23/166* (2013.01); *G01N 33/582* (2013.01); *C09K 11/06* (2013.01); *C09K 2211/1007* (2013.01); *C09K 2211/1011* (2013.01); *C09K 2211/1029* (2013.01)

(58) Field of Classification Search
CPC ..................... C09B 23/166; C09K 2211/1011; C09K 2211/1007; C09K 11/06; C09K 2211/1029; G01N 33/582
USPC .............................................. 514/342; 546/13
See application file for complete search history.

(56) References Cited

PUBLICATIONS

Dorwald "Side Reactions in Organic Synthesis: A Guide to Successful Synthesis Design" 2005 Wiley-VCH Verlag GmbH & Co. KGaA, Wienheim, Chapter 1.*
Araneda, J. F. et al; "High Stokes Shift Anilido-Pyridine Boron Difluoride Dyes" Angew. Chem. Int. Ed., vol. 50(51), Dec. 2011, pp. 12214-12217.
Ren, Y. et al; Boron Complexes with Chelating Anilido-Imine Ligands: Synthesis, Structures and Luminescent Properties:; Eur. J. Inorg. Chem.; (13), 2007, pp. 1808-1814.
(Continued)

*Primary Examiner* — John Mabry
*Assistant Examiner* — Daniel Carcanague
(74) *Attorney, Agent, or Firm* — Hill & Schumacher; Lynn C. Schumacher; Stephen W. Leonard

(57) ABSTRACT

Herein are disclosed fluorescent dyes based around a framework for a ligand comprising a pyridyl group linked to a diaryl anilido unit. A variety of ligands based on this framework are disclosed. The ligands chelate to a $BF_2$ center to produce the fluorescent dye. The disclosed dyes combine longer Stokes shifts (approximately 100 nm) with increased quantum yields. They are also photostable in aqueous and organic solutions for several hours. These dyes may be used in the labeling of biomolecules for bioimaging and assays. Also disclosed are methods for the synthesis of these dyes.

26 Claims, 12 Drawing Sheets

(56) References Cited

PUBLICATIONS

Liu, X. et al; Synthesis, structure and electroluminescent properties of Schiff-based boron complex with anilido-imine ligand:; J. Phys. Chem. Solids, vol. 70(1), 2009, pp. 92-96.

Liu, X. et al; "Synthesis, structure, photoluminescent and electroluminescent properties of boron complexes with anilido-imine ligands"; Inorganica Chemica Acta, vol. 363(7) 2010, pp. 1441-1447.

International Search Report, PCTCA2012/050544, dated Dec. 28, 2012, 3 pages.

* cited by examiner

| | $\lambda_{abs}$ | $\lambda_{em}$ | Stokes Shift | $\varepsilon_{max}$ | $\tau_f$ | $\chi^2$ | $\phi_f$ | $k_{nr}$ |
|---|---|---|---|---|---|---|---|---|
| | [nm] | [nm] | [nm] | [$M^{-1}cm^{-1}$] | [ns] | ($\tau_f$) | | [$10^8 s^{-1}$] |
| $1_H$-Dipp-$BF_2$ | 416 | 511 | 95 | 9640 | 6.9 | 1.03 | 0.29 | 1.0 |
| $1_{Me}$-Dipp-$BF_2$ | 419 | 515 | 96 | 10065 | 6.1 | 0.99 | 0.27 | 1.2 |
| $1_{Cy}$-Dipp-$BF_2$ | 418 | 518 | 100 | 10622 | 5.4 | 1.09 | 0.31 | 1.3 |
| $1_H$-Ph-$BF_2$ | 417 | 544 | 127 | 9529 | 2.0 | 0.98 | 0.33 | 3.4 |
| 2-Dipp-$BF_2$ | 466 | 569 | 103 | 5844 | 11.1 | 1.05 | 0.66 | 3.1 |
| 2-Ph-$BF_2$ | 465 | 584 | 119 | 9114 | 6.2 | 1.04 | 0.60 | 6.5 |
| $3_{tBu}$-$BF_2$ | 431 | 523 | 92 | 9772 | 5.8 | 1.06 | 0.62 | 6.6 |
| $3_H$-$BF_2$ | 416 | 496 | 80 | 11252 | 5.5 | 1.01 | 0.75 | 4.5 |
| BODIPY 1 | 517 | 538 | 21 | 64000 | 6.2 | --- | 0.83 | 0.3 |
| BODIPY 2 | 571 | 597 | 26 | --- | --- | --- | --- | --- |

Figure 2 linker = any aliphatic, aromatic or otherwise covalent linker

FLUORESCENT DYES WITH LARGE STOKES SHIFTS

This application is a national stage application of International Application No. PCT/CA2012/050544, filed Aug. 10, 2012, and claims benefits under 35 USC §119 of U.S. Provisional Application Ser. No. 61/522,829 filed Aug. 12, 2011, and the entire disclosures of the referenced applications are incorporated herein by reference.

FIELD OF THE INVENTION

The present disclosure relates to fluorophores having large Stokes shifts and high quantum yields, and their use in fluorescent dyes. Such dyes can be used to label biomolecules and for biological imaging and assays.

BACKGROUND

Certain molecules contain functional groups which can absorb and then emit photons. These groups are called fluorophores. A fluorophore absorbs photons of a specific wavelength and energy. Each photon absorbed excites one of the fluorophore's electrons into a higher energy state. The excited electron remains in its high-energy state for a few nanoseconds. While in its excited state, the electron dissipates a small amount of energy via interactions with the rest of the molecule or with the surrounding molecules. The electron then returns to its ground state energy, and, in doing so, emits a photon. This process is known as fluorescence. The emitted photon is of lower energy and hence longer wavelength than the incident photon, due to the dissipative loss of energy to the fluorophore's environment. The difference in energy (or wavelength) is called the Stokes shift.

The Stokes shift is fundamental to fluorescence detection because it allows the small numbers of emission photons to be isolated from the large number of incident excitation photons. For dyes with a small Stokes shift, the excitation and emission spectra have significant overlap, resulting in quenching. Quenching occurs when an emitted photon is reabsorbed by an adjacent fluorophore before it returns to the ground state. Furthermore, an excited electron may also lose its energy via dissipative effects such as vibration. As such, the number of emitted photons may not equal the number of incident photons, reducing the overall signal from the sample. The loss of signal may be quantified by the quantum yield, which is the ratio of emitted photons to incident photons. Generally, the same fluorophore can be repeatedly excited and relaxed, and a single fluorophore can generate many thousands of detectable photons. This allows very sensitive fluorescence detection techniques. However, some fluorophores may be destroyed in the excited state, leading to photobleaching which also has important applications.

The great benefit of fluorescent molecules comes when they are conjugated with biomolecules and used as fluorescent labels for biological imaging or assays. Possible conjugations are proteins, nucleotides, enzymes, fatty acids, phospholipids and receptor ligands. Tissues or cells, containing biomolecules conjugated with fluorophores, can be viewed under a fluorescent microscope. Fluorescent gels and blots can be quantified using a fluorescence scanner. Fluorescent cells or particles can be counted using flow cytometry.

BODIPY dyes are widely used fluorescent dyes that combine a dipyrrinato ligand with a $BF_2$ core, which serves to rigidify the fluorophore, leading to high quantum yields. However, the symmetry of the dye structure results in low Stokes shifts. The core structure has a green fluorescence, but substitutions onto the parent molecule allow 7 different colours from green to red. BODIPY dyes can be readily conjugated with a variety of biomolecules. BODIPY systems have recently displaced common fluorophores such as rhodamine and fluorescein, due to the ease of manipulating their electronic properties. However, one of the problems that has not been circumvented with these systems is the small Stokes shift. Several modifications in the structure have been made either in the ligand or to the atoms attached to boron, but better solutions are still being pursued.

SUMMARY

Herein is disclosed a fluorophore shown by the following formula, or a salt thereof,

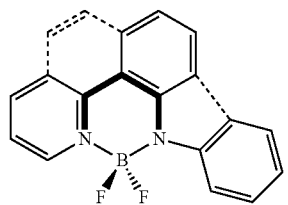

wherein bonds indicated by dotted lines may be independently present or absent; and wherein each hydrogen atom may be independently substituted by a moiety.

Herein is also disclosed a fluorophore shown by the following formula, or a salt thereof,

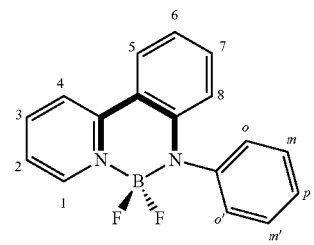

wherein each hydrogen atom may be independently substituted by a moiety.

Herein is also disclosed a fluorophore shown by the following formula, or a salt thereof,

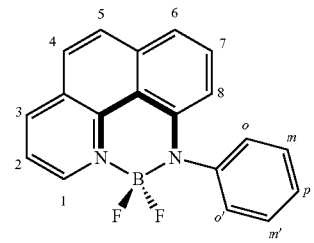

wherein each hydrogen atom may be independently substituted by a moiety.

Herein is also disclosed a fluorophore shown by the following formula, or a salt thereof,

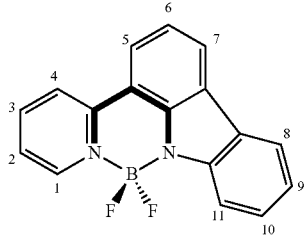

wherein each hydrogen atom may be independently substituted by a moiety.

In various embodiments, a moiety is selected from the group consisting of:

alkyl, optionally substituted with 1 to 5 functional groups, each substitution being made independently of any other substitution;

aryl, optionally substituted with 1 to 3 functional groups, each substitution being made independently of any other substitution;

heteroaryl, optionally substituted with 1 to 3 functional groups, each substitution being made independently of any other substitution;

arylalkyl or heteroarylalkyl, each optionally substituted with 1 to 3 functional groups, each substitution being made independently of any other substitution; and a functional group.

In an embodiment, the invention is a fluorophore, or a salt thereof, shown by any one of formulas (2'), (3') and (4'),

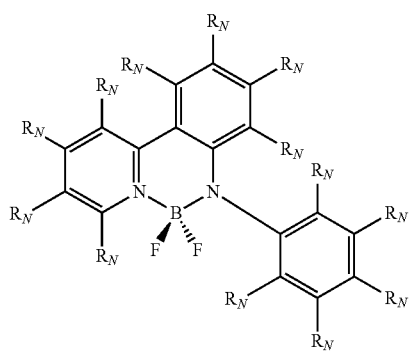

(2')

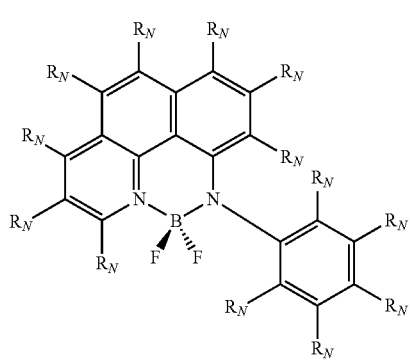

(3')

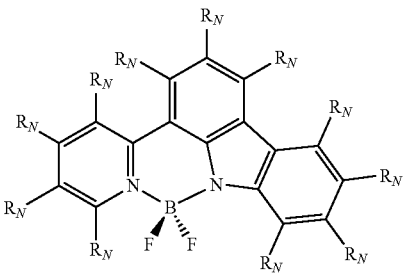

(4')

wherein each of $R^N$ individually represents either an H or a monovalent organic group. Examples of the monovalent organic groups are alkyl, aryl, heteroaryl, arylalkyl and heteroarylalkyl as defined herein. Any of the monovalent organic groups can be functionalized i.e. include a functional group described herein.

Herein is also disclosed a method of producing a fluorophore shown by the following formula,

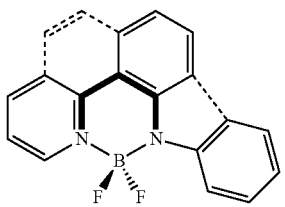

said method comprising the steps of
synthesizing a ligand capable of chelating to a $BF_2$ center, mixing said ligand with a solution of triethyl amine, and adding boron trifluoride etherate to said solution.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIG. 2 is a table that summarizes the properties of certain embodiments of the disclosed dyes in comparison to two common prior art BODIPY derivatives. Note that the absorption wavelength ($\lambda_{abs}$) is the longest absorption maximum, and the emission wavelength ($\lambda_{em}$) is the emission maximum upon excitation at the absorption wavelength. Also note that the absolute quantum yield ($\phi_f$) was determined by a calibrated integrating sphere system. η indicates the fluorescence lifetime.

DETAILED DESCRIPTION

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in this specification including claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately", when used in conjunction with ranges of dimensions of particles, compositions of mixtures or other physical properties or characteristics, are meant to cover slight variations that may exist in the upper and lower limits of the ranges of dimensions so as to not exclude embodiments where on average most of the dimensions are satisfied but where statistically dimensions may exist outside this region. It is not the intention to exclude embodiments such as these from the present disclosure.

As used herein, the term "Stokes shift" means the difference in the wavelength of the highest absorption peak at the longest wavelength of a compound and the wavelength of the emission peak of the compound. The Stokes shift may equivalently be stated in terms of the frequency of the absorption and emission peak, or the energy of the absorption and the emission peak.

Figure 1:
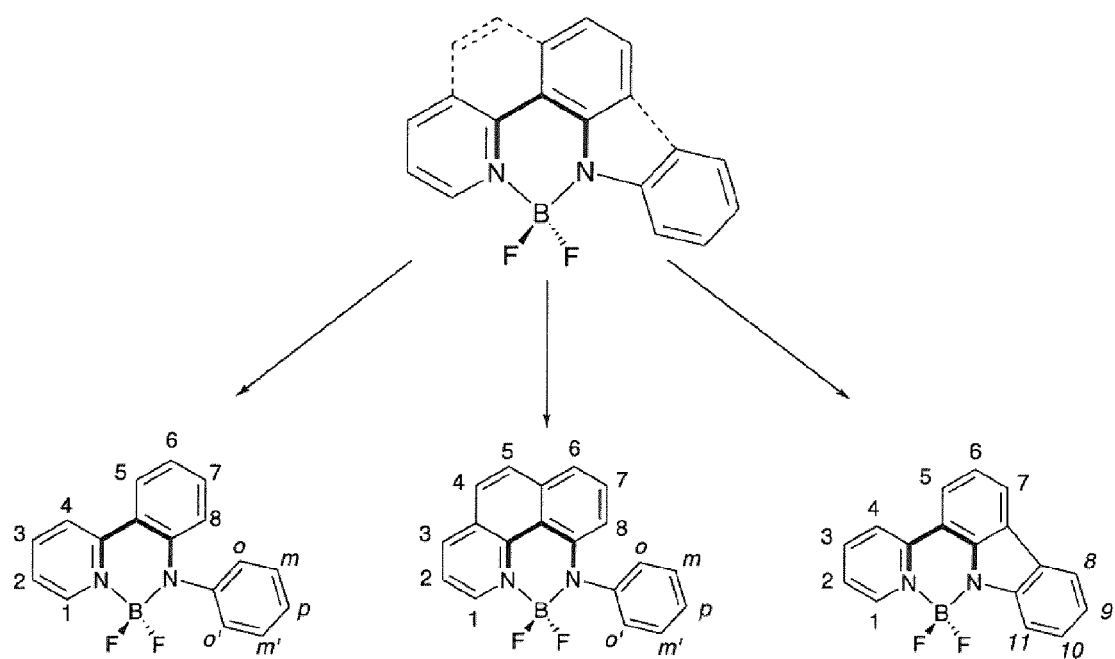
FIG. 1 shows the chemical structure of certain embodiments of the disclosed dyes.
Figure 19:
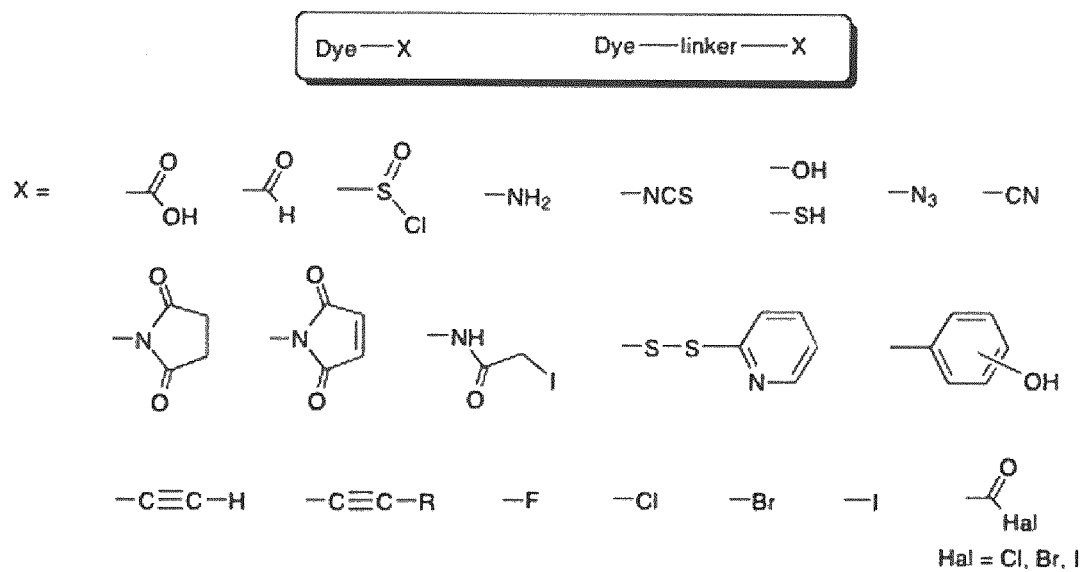
FIG. 19 shows the chemical structure of a variety of functional groups or moieties that may be affixed to the disclosed dyes to enable linking of the disclosed dyes to proteins and other biomolecules.

As used herein, the term "moiety" means a monovalent radical present in one of the labeled positions of one of the framework molecules having a structural formula shown in FIG. 1. In other words, such a moiety takes the place of a hydrogen atom at one of the indicated positions of a framework molecule. More than one moiety may be included in a particular molecule. The moiety may or may not include i.e., contain one or more functional groups, such as the "X-groups" shown in FIG. 19. The groups having structures shown in FIG. 19 are identified in the text herein as carboxyl (—CO$_2$H), formyl (—C(O)H), chlorosulfinyl (—S(O)Cl), amino (—NH$_2$), hydroxyl (—OH), thiol or sulfhydryl (—SH), azide (—N$_3$), cyano (—CN), 1-yl-2,5-pyrrolidinedione, (—NC$_4$H$_4$O$_2$), 1-yl-pyrrole-2,5-dione (—NC$_4$H$_2$O$_2$), N-yl-iodoacetamide (—NHC(O)CH$_2$I), 2-pyridinyl-disulfidyl (—S—S-py; py=2-pyridinyl), hydroxyphenyl (—C$_6$H$_4$—OH), ethynyl (—C≡CH), substituted ethynyl (—C≡CR), fluoro (—F), chloro (—Cl), bromo (—Br), iodo (—I), halocarbonyl (—C(O)hal; hal=chlorine, bromine, iodine).

An "alkyl" group is a linear, branched or cyclic monovalent hydrocarbon radical. A linear alkyl group has 1 to 20 carbon atoms, preferably 1 to 12, or 1 to 10, or 2 to 10 or 4 to 10 carbon atoms and more preferably 1 to 8 or 1 to 6 or 2 to 8 or 4 to 8 carbon atoms, or 1 to 4 carbon atoms or 1, 2, 3, 4, 5, 6, 7, 8, 9 or 10 carbon atoms. A branched or cyclic hydrocarbon has 3 to 20 carbon atoms, preferably 3 to 12 carbon atoms and more preferably 3 to 8 carbon atoms, or 3, 4, 5, 6, 7, 8, 9 or 10 carbon atoms. For any use of the term "alkyl," unless clearly indicated otherwise, it is intended to embrace all variations of alkyl groups disclosed herein, as measured by the number of carbon atoms, the same as if each and every alkyl group was explicitly and individually listed for each usage of the term. The same is true for other groups listed herein, which may include groups under other definitions, where a certain number of atoms is listed in the definition. When an alkyl group is cyclic, it may also be referred to as a cycloalkyl group. A cycloalkyl group may have 3, 4, 5, 6 or 7 carbon atoms in the cyclic portion(s). When an alkyl residue having a specific number of carbons is named, all geometric isomers having that number of carbons are intended to be encompassed; thus, for example, "butyl" is meant to include n-butyl, sec-butyl, iso-butyl and t-butyl.

An "aryl" group is a monocyclic, bicyclic or tricyclic aromatic ring structure. An aryl group is preferably a 6-membered aromatic. Examples of groups whose radicals are aryl groups include e.g., benzene, naphthalene, indane, tetralin.

A "heteroaryl" group is an aryl group, preferably a 5- or 6-membered aromatic, containing 1 to 3 annular heteroatoms selected from O, N, or S. Examples of groups whose radicals are heteroaryl groups include e.g., imidazole, pyridine, indole, thiophene, benzopyranone, thiazole, furan, benzimidazole, benzoxazole, benzthiazole, quinoline, isoquinoline, quinoxaline, pyrimidine, pyrazine, tetrazole and pyrazole.

It should be noted here, that when discussing radical portions or individual atoms of a molecule or other moiety, connecting bonds may be omitted, and the skilled person understands this. For example, in the substituted phenyl group, —C$_6$H$_3$R, connecting bonds of R are omitted or included in various contexts for the sake of convenience.

As used herein, the term "fluorescent lifetime" when used in reference to a fluorophore means the average time between when the fluorophore absorbs a photon and when the fluorophore emits a photon.

Herein are disclosed a set of BF$_2$ dyes based on a pyridyl-anilido structure shown in formula (I). The dyes comprise a pyridyl-anilido ligand that chelates the BF$_2$ center. The ligand may be variously modified, as described below, to yield a variety of embodiments.

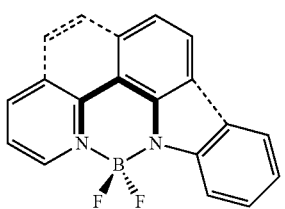
(I)

Figure 3:
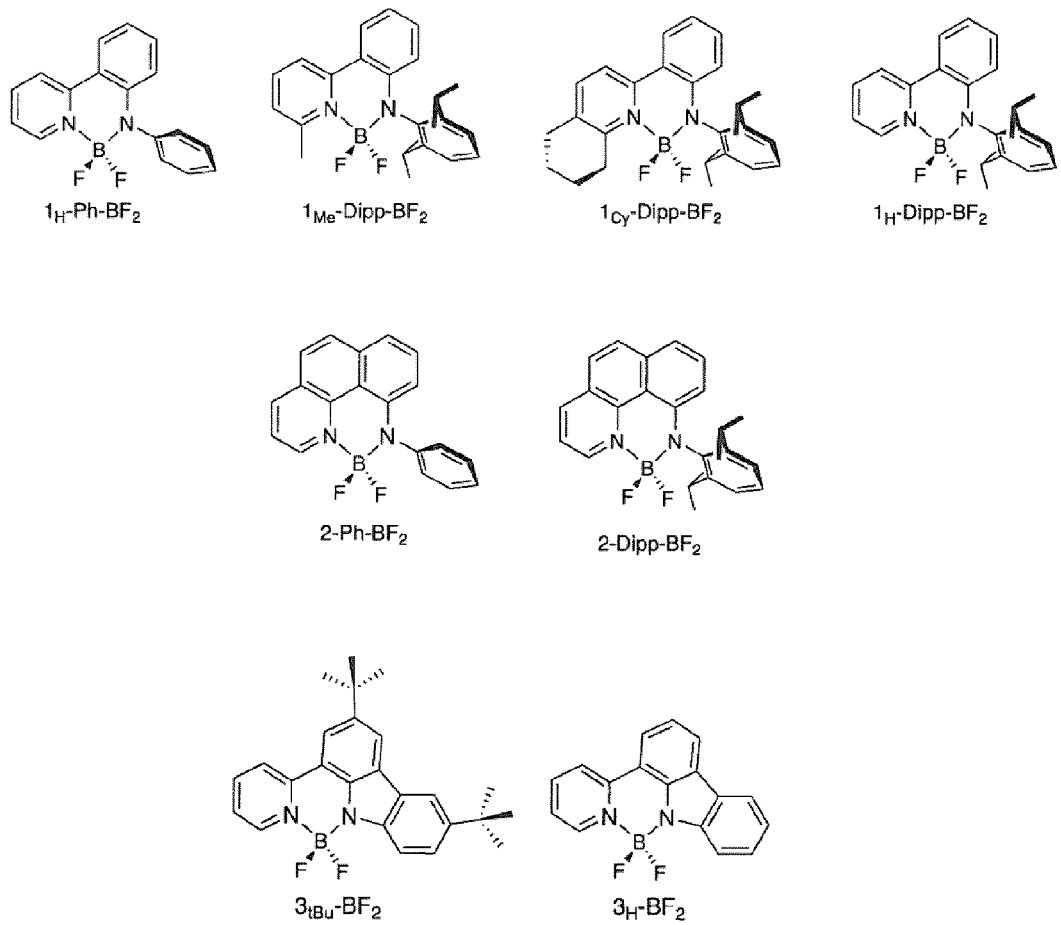
FIG. 3 shows the chemical structure of a variety of embodiments of the disclosed dyes.

The disclosed dyes feature ligands that lack the symmetry generally found in existing BODIPY dyes. Without being bound by theory, it is believed that this lack of symmetry leads to a longer Stokes shift than BODIPY dyes. The disclosed dyes are also rigidified in order to reduce vibrational energy loss. Without being bound by theory, it is believed that such rigidification increases the quantum yield of the dye. Several classes of embodiments are possible, wherein each class has the bonds indicated by dotted in lines in formula (I) independently present or absent. Each of these classes contains particular embodiments with various substituents linked to the carbon rings. FIG. 3 shows the chemical structure of a variety of embodiments of the disclosed dyes. The dyes embodied by these chemical structures in FIG. 3 may be variously configured with a variety of substituents and functional groups, as described below. In embodiments, a fluorophore shown by formula (I) has a Stokes shift of from about 70 nm to about 140 nm or about 80 nm to about 130 nm.

One class of embodiments of the disclosed dyes has a parent structure comprising a pyridyl group linked to the aryl anilido unit which chelates the BF$_2$ center, as shown in formula (II).

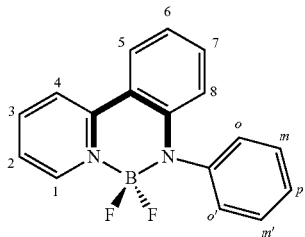
(II)

Substitution around the periphery of the ligand shown in formula (II) may be made in one or more of positions 1-8. FIG. 19 shows non-limiting examples of a variety of substituents that may be installed in one or more of positions 1-8. In embodiments, a fluorophore shown by formula (II) has a Stokes shift of from about 95 nm to about 105 nm or about 122 nm to about 132 nm. In particular embodiments, alkyl groups are installed in positions 1 or 2.

Substitutions in positions 6 and 7 may also be made. For instance, starting the synthesis of the ligands from commercially available 2-fluoro-4-methylphenylboronic acid and 2-fluoro-5-methylphenylboronic acid results in substitutions in positions 6 and 7, respectively. Substitutions in positions 1, 2, and 3 may be made starting from commercially available 2-bromo-6-methylpyridine, 2-bromo-5-methylpyridine, and 2-bromo-4-methylpyridine, respectively. The methyl groups thus installed may be oxidized later in the synthesis to install carboxylic acids. The N-aryl group can be decorated in all positions o, o', m, m', and p. Particular embodiments feature substituents in positions o/o' and m/m'. Particular examples of the dyes embodied by formula (II) are 1$_H$-Dipp-BF$_2$, 1$_{Me}$-Dipp-BF$_2$, 1$_{Cy}$-Dipp-BF$_2$, and 1$_H$-Ph-BF$_2$, the chemical structures of which can be seen in FIG. 3. These embodiments are fluorescent under UV irradiation. Quantitative assessment of the UV/Vis and fluorescent properties were performed in dichloromethane under oxygen-free conditions.

Figure 4:
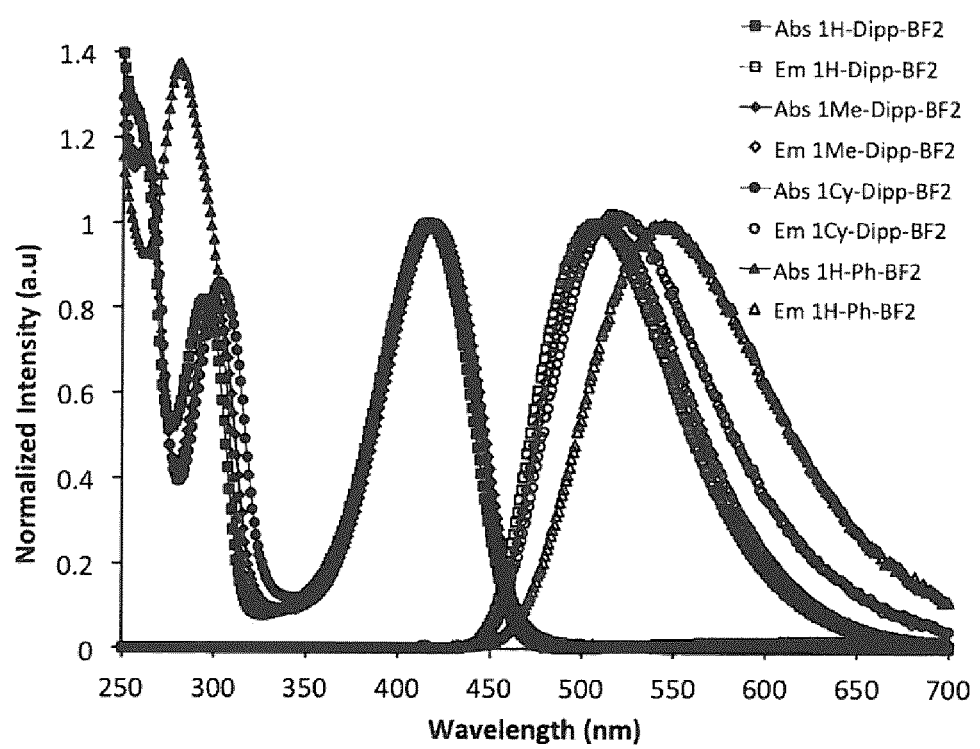
FIG. 4 is graph showing the absorption and emission spectra of certain embodiments ($1_H$-Dipp-$BF_2$, $1_{Me}$-Dipp-$BF_2$, $1_{Cy}$-Dipp-$BF_2$, and $1_H$-Ph-$BF_2$) of the disclosed dyes.

FIG. 4 shows the absorption and emission profiles for the compounds. In solution the complexes are light yellow and give green emission. The absorption spectra for all the complexes based on formula II are very similar with a maximum absorption at 416 nm, 419 nm, 418 nm, and 417 nm for 1$_H$-Dipp-BF$_2$, 1$_{Me}$-Dipp-BF$_2$, 1$_{Cy}$-Dipp-BF$_2$, and 1$_H$-Ph-BF$_2$, respectively (FIG. 4). The emission maximum were found at 511 nm for 1$_H$-Dipp-BF$_2$, 515 nm for 1$_{Me}$-Dipp-BF$_2$, 518 nm for 1$_{Cy}$-Dipp-BF$_2$, and 536 nm for 1$_H$-Ph-BF$_2$ (FIG. 4). The compounds based on formula II exhibit excellent Stokes shifts, but only moderate quantum yields. Without being bound by theory, this may be due to the lack of structural rigidity in the dye, which allows more non-radiative relaxation paths to be operative.

The compounds exemplified by formula (III) rigidify the ligand more effectively. Without being bound by theory, it is believed that the quantum yield of the emission can be enhanced by closing the aromatic rings in the ligands to produce more planar complexes and reduce the degrees of freedom with respect to the bond wagging. The compounds based on formula (III) contain a rigidified ligand bridged by an ethynyl group in positions 4 and 5 of formula (II).

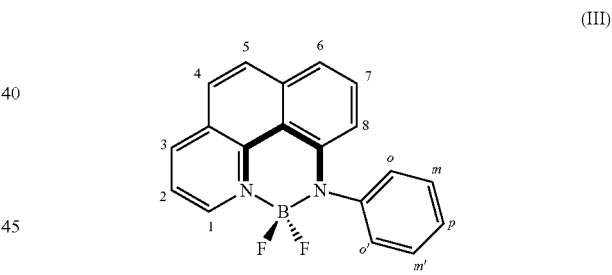
(III)

This reduces energy loss via vibrational relaxation and increases the emission efficiency. Furthermore, extension of the π-electron system also generally leads to elevation in the fluorescence quantum yield. Increased conjugation also decreases the energy difference between the ground state and the excited state, producing a red shift in the absorption and emission profiles. This is desirable in molecules and complexes used to label proteins or study organisms because longer wavelength emissions are less energetic and produce less tissue damage. Furthermore, cellular or tissue components exhibit low absorption and autofluorescence in the near IR. In embodiments, a fluorophore shown by formula (III) has a Stokes shift of from about 98 nm to about 108 nm or about 114 nm to about 124 nm.

Particular embodiments of the dye shown in formula (III) include compounds substituted in one or more of positions 1-8, as well as the o, o', m, m', and p positions on the N-aryl group. FIG. 19 shows non-limiting examples of a variety of substituents that may be installed in one or more of these positions. Position 6 may be modified starting from known 5-methylbenzo[h]quinoline. Position p may be functionalized if 4-iodo-aniline is modified before the amination reaction.

Figure 5:
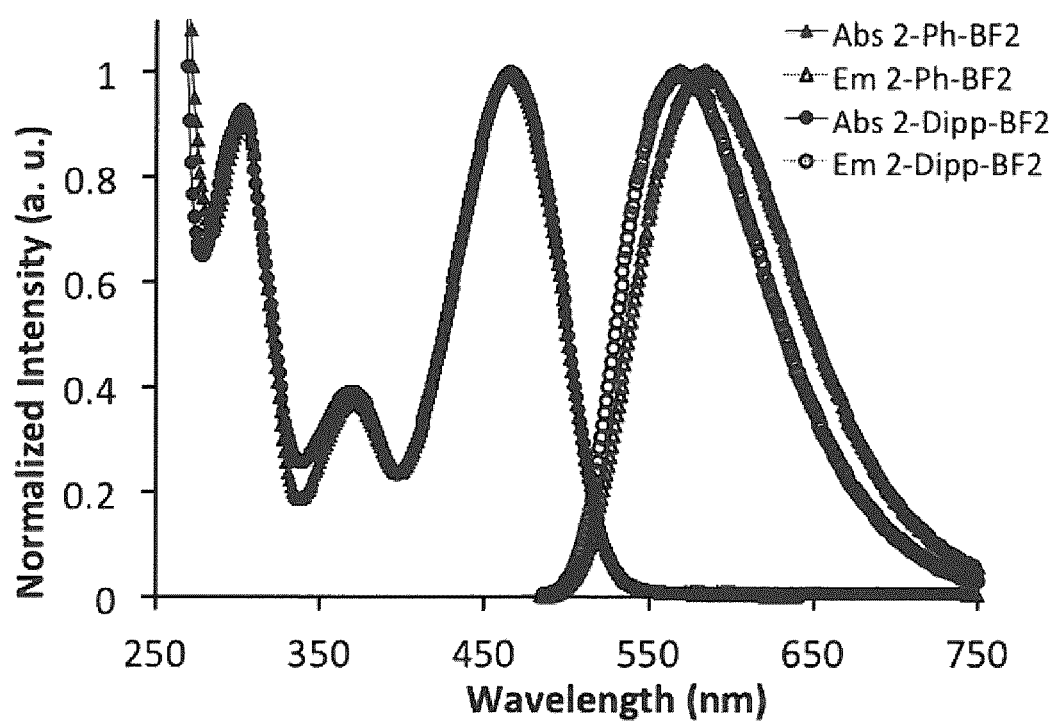
FIG. 5 is graph showing the absorption and emission spectra of certain embodiments (2-Ph-$BF_2$ and 2-Dipp-$BF_2$) of the disclosed dyes.

Two particular embodiments based on formula (III) are 2-Ph-BF$_2$ and 2-Dipp-BF$_2$, the chemical structures of which can be seen in FIG. 3. These dyes are fluorescent under UV irradiation. As can be seen in FIG. 5 and FIG. 2, they also have an enhanced quantum yield while maintaining the large Stokes shift. Without being bound by theory, it is believed that by closing the aromatic rings in the ligand, the absorption and emission spectra are red-shifted due to a smaller energy difference between the HOMO and LUMO orbitals. In solution both complexes are slightly orange, but under UV light (254 nm) the solutions turn an intense orange color (FIG. 5). In 2-Ph-BF$_2$, the non-radiative decay rate constant increased and the fluorescence lifetime decreased considerably. Fluorescence lifetime data were consistently well-described by a single exponential. As observed in the dyes based on formula (II), the absorption spectra are very similar, but the emission spectrum is slightly red-shifted for the complex bearing the N-phenyl unit, 2-Ph-BF$_2$. The formation of an excited state accompanied by an increase in the dipolar moment of the molecule can be used to explain this behavior as in the 2-(2-pyridyl)-N-arylanilido derivatives.

Based on the same principle applied to develop the formula (III) dyes, the N-aryl rings in the 2-(2-pyridyl)-N-arylanilido complexes were joined to produce dyes represented by formula (IV). The dyes based on formula (IV) demonstrated an increased quantum yield compared to the ones based on formula (II).

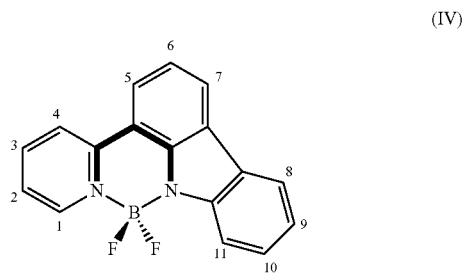

(IV)

Figure 6:
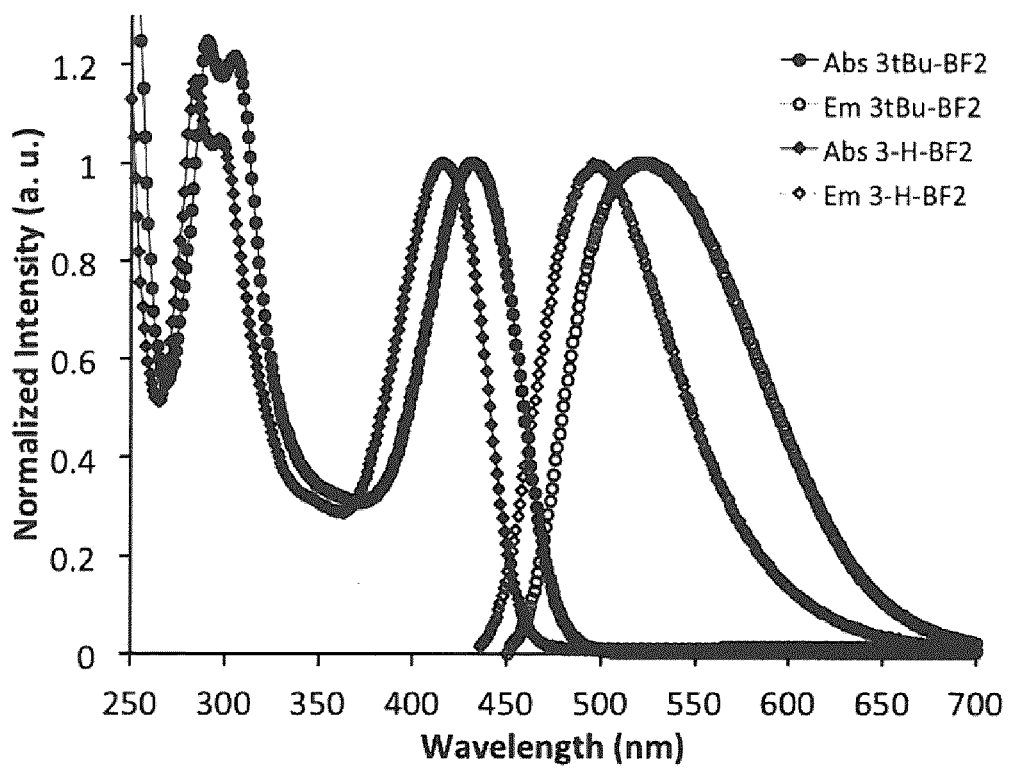
FIG. 6 is graph showing the absorption and emission spectra of certain embodiments ($3_{tBu}$-$BF_2$ and $3_H$-$BF_2$) of the disclosed dyes.

Formula (IV) encompasses dyes that comprise a pyridyl anilido ligand in which the anilido portion is based on the carbazole unit, formed by forging a C—C bond between positions 8 and o of formula (II). Various embodiments of the formula (IV) dyes are possible by the substitution of various groups in all positions 1-11. FIG. 19 shows non-limiting examples of a variety of substituents that may be installed in one or more of positions 1-11. In embodiments, a fluorophore shown by formula (IV) has a Stokes shift of from about 87 nm to about 97 nm or about 75 nm to about 85 nm. Particular embodiments comprise the structure of formula (IV) with substituents in positions 6 and 9. Substitutions on positions 1, 2 and 3 may also be made using commercially available 6-methyl-2-pyridylzinc bromide, 5-methyl-2-pyridylzinc bromide, and 4-methyl-2-pyridylzinc bromide for the Negishi coupling reaction. Particular embodiments of the compounds represented by formula (IV) include 3$_{tBu}$-BF$_2$ and 3$_H$-BF$_2$, the chemical structure of which can be found in FIG. 3. In the solid state, these complexes are completely planar, with the boron atom in the same plane as the ligand framework. The two B—N bonds have disparate lengths, leading to the asymmetry of the complex that is, without being bound by any specific theory, thought to be desirable for the large Stokes shift. The particular embodiments of formula (IV), 3$_{tBu}$-BF$_2$ and 3$_H$-BF$_2$, are yellow in solution and emit bright green with an emission maxima at 491 nm for 3$_{tBu}$-BF$_2$ and 470 for 3$_H$-BF$_2$ (FIG. 6 and FIG. 2). The quantum yield increased from around 0.30 in the formula (II) dye complexes to 0.62 in 3$_{tBu}$-BF$_2$ and to 0.75 in 3$_H$-BF$_2$, comparable values to those of the formula (III) complexes and following the expected behaviour when the degree of conjugation and the rigidity are increased. Large Stokes shift and reasonable lifetime were retained.

Another embodiment of the dyes disclosed herein has the combined structural features of formulae (III) and (IV), in which a C—C bond between positions 8 and o of formula (III) is forged. Various substituents may be installed on this dye, as well. Exemplary substituents are shown in FIG. 19.

The families of dyes disclosed herein are characterized by their large Stokes shift of approximately 100 nm, photostability in both aqueous and organic solutions for several hours, quantum yields of 0.6 or higher. The disclosed dyes are also solvatochromatic.

Figure 7:
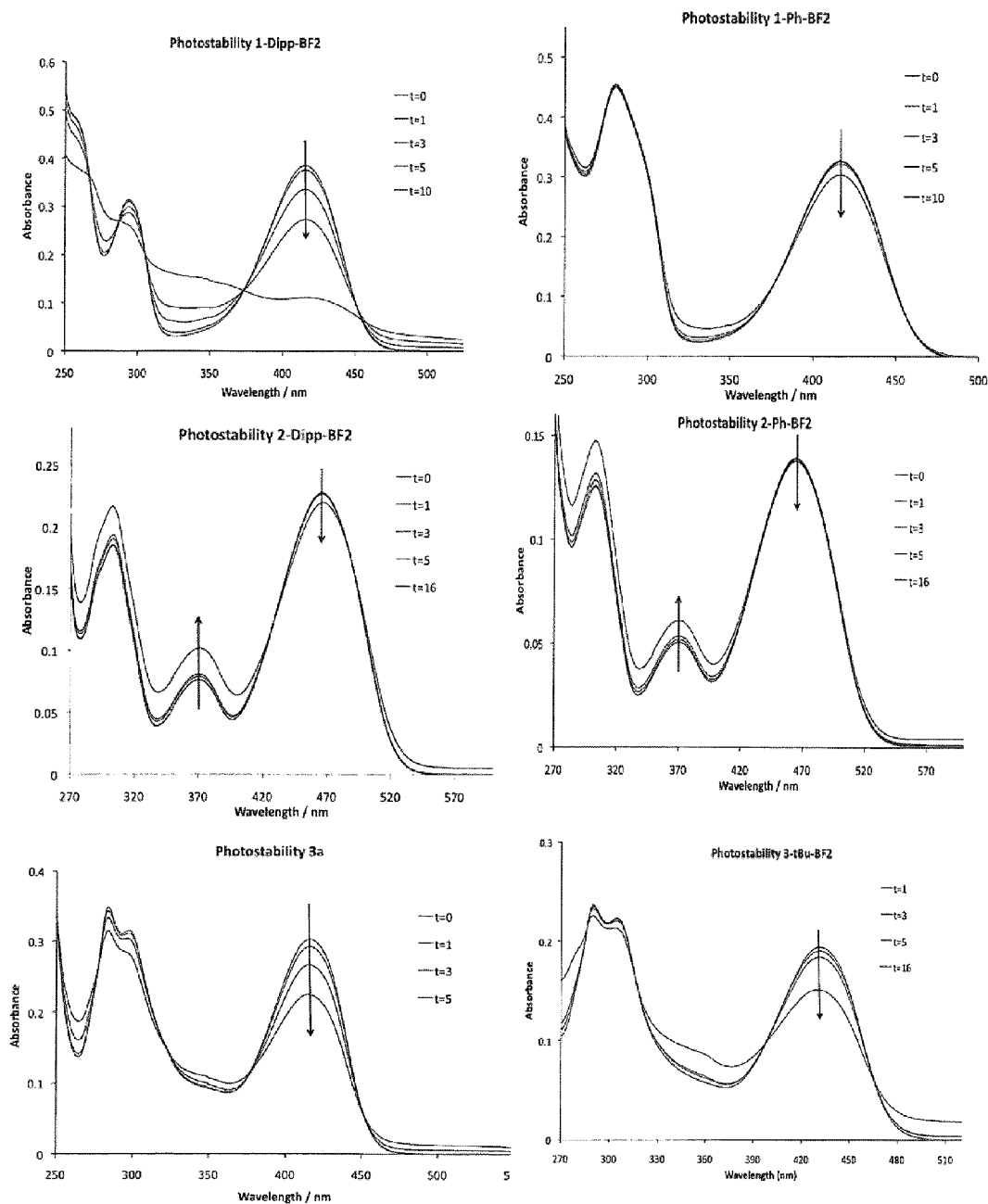
FIG. 7 is a set of graphs showing the change in absorption spectrum over time of a variety of embodiments of the disclosed dyes after irradiation at 420 nm wavelength.

Photostability studies showed all three families of dyes are significantly more stable than prior art BODIPY derivatives and rhodamine 101. Photostability studies were performed in non-deoxygenated dichloromethane solutions of the dyes and the change in the absorption spectra were recorded at different intervals after irradiation of the samples with 420 nm wavelength. FIG. 7 shows the decrease in absorption intensity over time for several of the dyes disclosed herein.

The disclosed dyes may be substituted to enable linking to biomolecules. FIG. 19 shows the chemical structure of several exemplary and non-limiting functional groups that may be substituted onto the disclosed dyes to enable the disclosed dyes to link to proteins and other biomolecules, though those skilled in the art will recognize that other functional groups may be equivalent used. The dyes may be attached to biomolecules using specific functional groups such as amino groups, carbonyl or carboxyl groups, thiol, or azide groups. Particular examples of moieties for attaching to e.g. proteins include succinimide, isothiocyanate, hydrazine, carbodiimide, acetyle bromide and maleimide. The dyes may also be attached non-covalently to biomolecules. Those skilled in the art will recognize that the disclosed functional groups may be variously modified and still allow linking to biomolecules. Possible biomolecular targets include proteins, nucleotides, enzymes, fatty acids, phospholipids and receptor ligands. They may be used as fluorescent labels for biological imaging or assays. Tissue or cells labeled thus may be viewed under a fluorescence microscope. Cells or particles labeled thus may be counted using flow cytometry. Fluorescent gels and blots may be quantified using a fluorescence scanner.

The disclosed dyes have multiple nanosecond lifetimes (as shown in FIG. 2) and may also be useful in fluorescence polarization assays to examine interactions between proteins and other biological molecules or in fluorescence lifetime experiments (e.g., fluorescence lifetime imaging microscopy, FLIM) where longer lifetime dyes can be used to reveal additional information about a particular biological sample.

The following examples are presented to enable those skilled in the art to understand and to practice embodiments of the present disclosure. They should not be considered as a limitation on the scope of the present embodiments, but merely as being illustrative and representative thereof.

EXAMPLES

The following describes the synthesis of the specific embodiments of the disclosed dyes presented in FIG. 3.

Synthesis of 2-(2-fluorophenyl)-pyridine and its Derivatives

Figure 8:
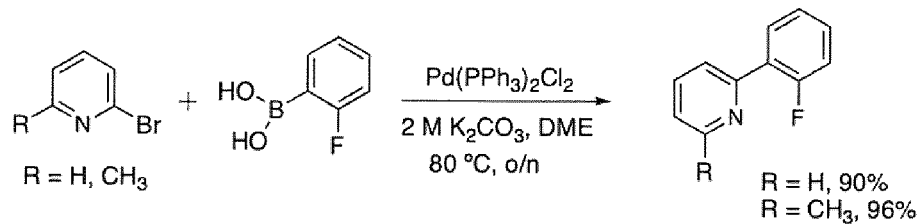
FIG. 8 is a scheme showing the synthesis of 2-(2-fluorophenyl)-pyridine.

The synthesis of 2-(2-fluorophenyl)-pyridine has been previously reported through a Suzuki-Miyaura coupling reaction, utilizing 2-fluorophenylboronic acid and 2-bromopyridine. The reaction proceeds to completion after 12 hours at 80° C. in a mixture of DME and an aqueous 2 M solution of potassium carbonate. The same protocol was used to prepare the 2-(2-fluorophenyl)-6-methylpyridine precursor from 2-fluorophenylboronic acid and 2-bromo-6-methylpyridine (FIG. 8). Both products are viscous yellow-orange liquids purified by flash chromatography.

Figure 9:
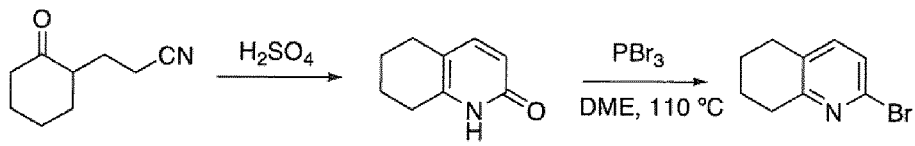
FIG. 9 is a scheme showing the synthesis of 2-bromo-5,6,7,8-tetrahydroquinoline.

The synthesis of the more complex precursor 2-(2-fluorophenyl)-5,6,7,8-tetrahydroquinoline required synthesis of 2-bromo-5,6,7,8-tetrahydroquinoline using the method of Zimmerman and Meyers (FIG. 9).

Figure 10:
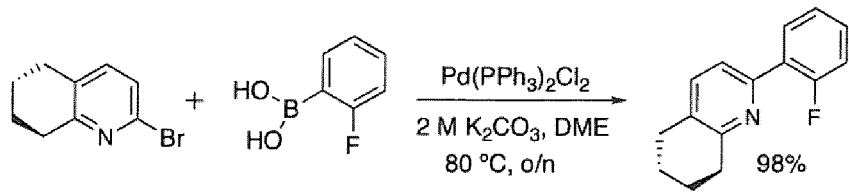
FIG. 10 is a scheme showing the synthesis of 2-(2-fluorophenyl)-5,6,7,8-tetrahydroquinoline.

Subsequently, Suzuki-Miyaura conditions were applied as in FIG. 8 using 2-bromo-5,6,7,8-tetrahydroquinoline and 2-fluorophenylboronic acid to obtain the 2-(2-fluorophenyl)-5,6,7,8-tetrahydroquinoline precursor as depicted in FIG. 10. After isolation and purification by flash chromatography, this viscous yellow-orange liquid solidifies at room temperature. In general, 2-(2-fluorophenyl)-pyridine derivatives wore prepared in high yields (over 92%).

Synthesis of 2-(2-pyridyl)-N-arylaniline Compounds

Figure 11:
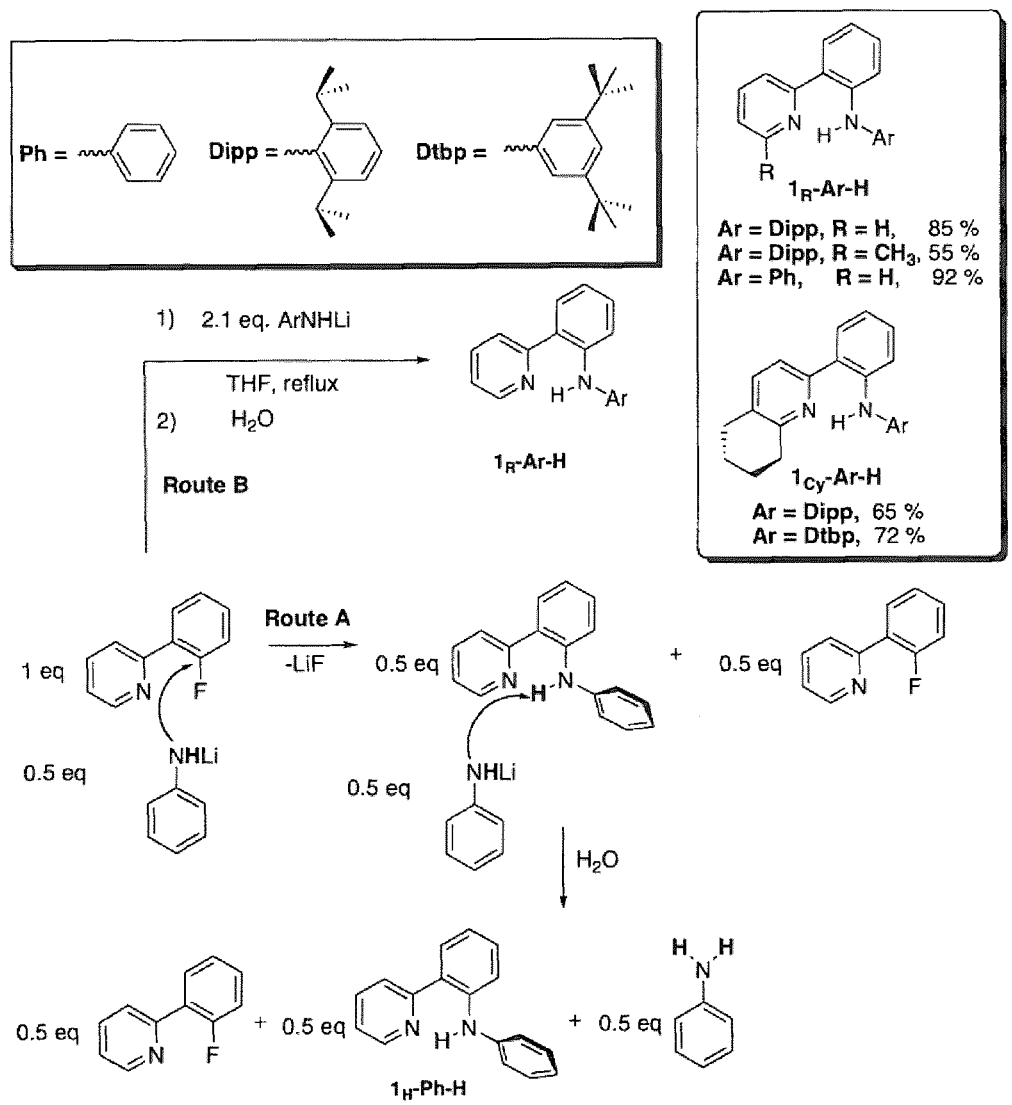
FIG. 11 is a scheme showing the synthesis of 2-(2-pyridyl)-N-arylaniline.

The aniline fragment in the target compounds was installed via nucleophilic aromatic substitution of fluoride using an established protocol. Use of two equivalents of lithium anilide was required in order to achieve acceptable yields since deprotonation of the newly formed ligand competed with the desired nucleophilic aromatic substitution. This protocol is shown in FIG. 11 for the range of ligands prepared; the reason for the need of the extra equivalent of anilide is also shown. The aniline by-product may be recovered in larger scale reactions.

The 2-(2-pyridyl)-N-arylaniline compounds were obtained as analytically pure yellow solids upon recrystallization from hot methanol. The compounds were characterized by $^1$H and $^{13}$C NMR spectroscopy. This modular synthesis allows for a wide array of ligands to be generated depending on the N-aryl substituents utilized. In addition to the 2,6-dialkyl aniline derivative, a less sterically demanding, 1$_H$-Ph-H, was prepared using aniline in 92% yield. Unlike the previous 2-(2-pyridyl)-N-arylaniline compounds, 1$_H$-Ph-H was isolated as a yellow liquid. None of the 2-(2-pyridyl)-N-arylaniline compounds displayed fluorescence upon irradiation with UV light (254 nm).

Introduction of ligands onto metal complexes is commonly achieved using lithium salts of the desired ligands and metal halides, since the formation of LiX (X=Br, Cl, I) provides the driving force to overcome the energy barrier associated with such reactions. For this reason it was decided to prepare and isolate the lithium salt, 1$_H$Dipp-Li. Addition of n-BuLi to a toluene solution of the proteo ligand at −78° C., followed by stirring at room temperature, yielded an orange solution with a solid in suspension. This solid was washed with hexanes and dried under vacuum to give a yellow solid in 86% yield. $^1$H-NMR spectrum showed the resonances for the ligand without the amine proton resonance, which is indicative of formation of Li—N bond. Lithium incorporation was confirmed by $^7$Li NMR, with a chemical shift of −0.59 ppm relative to LiCl. This chemical shift is in agreement with previously reported lithium complexes supported by mono anionic N—N ligands. X-ray quality crystals of 1$_H$Dipp-Li were grown by layering a THF solution of the complex in hexanes at −35° C.

In this complex the lithium atom is chelated by the deprotonated ligand forming a six membered ring. Two molecules of THF are coordinated to the Li cation, which exhibits a distorted tetrahedral geometry. The Li—N2 distance is slightly shorter than the Li—N1 (1.958(3)° and 2.002(3)°, respectively) illustrating the asymmetry of the ligand binding and consistent with a Li—N2 covalent bond and a Li—N2 dipolar bond.

Synthesis of 10-(N-arylamine)benzo[h]quinoline Compounds

Figure 12:
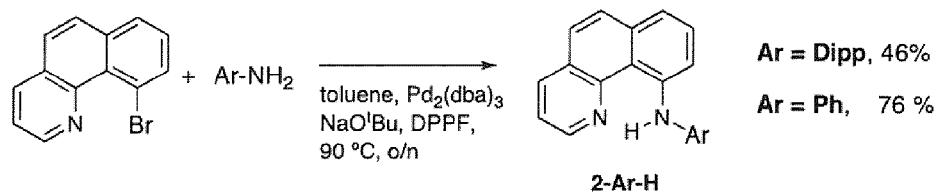
FIG. 12 is a scheme showing the synthesis of 2-Ph-H and 2-Dipp-H.

The straightforward synthesis of 2-Ph-H and 2-Dipp-H is outlined in FIG. 12. The 10-bromobenzo[h]quinoline required to accomplish the Buchwald-Hartwig amination was prepared according to a known procedures.

The coupling reaction was carried out in toluene using Pd$_2$(dba)$_3$ as the catalyst precursor and the desired aniline at 90° C. overnight. After the reaction was completed the solution turned dark with an intense yellow coloration. Both compounds were isolated as yellow solids. 2-Ph-H was synthesized in good yield (76%), but when 2,6-diisopropylaniline was used to produce 2-Dipp-H, the yield decreased considerably (46%). Even over increased periods of time, no significant change in the yield was observed. This result is most likely a consequence of the steric hindrance afforded by the bulky 2,6-diisopropyl groups, diminishing the coordination of the amine to the palladium center. Neither 2-Ph-H nor 2-Dipp-H displayed fluorescence upon irradiation with UV light (254 nm). For 2-Dipp-H the $^1$H NMR displayed the characteristic resonance for the 2,6-diisopropyl groups and both ligands showed the amine proton shifted down field. The aromatic region of the $^1$H NMR spectrum was complicated by the overlap of some signals; nevertheless it was fully assigned using 2D experiments.

Synthesis of 1-(2-pyridyl)-9H-carbazole Compound

Figure 13:
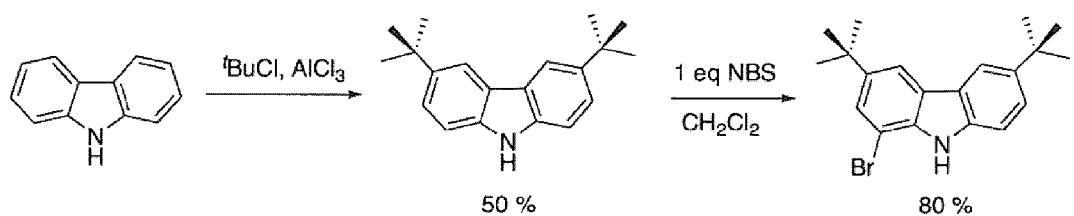
FIG. 13 is a scheme showing the synthesis of 1-bromo-3,6-di-tert-butyl-9H-carbazole.

The reaction of 3,6-di-tert-butyl-9H-carbazole with NBS produced 1-bromo-3,6-di-tert-butyl-9H-carbazole as a white-glassy solid in 80% yield after purification by flash chromatography on silica gel (FIG. 13).

Figure 14:
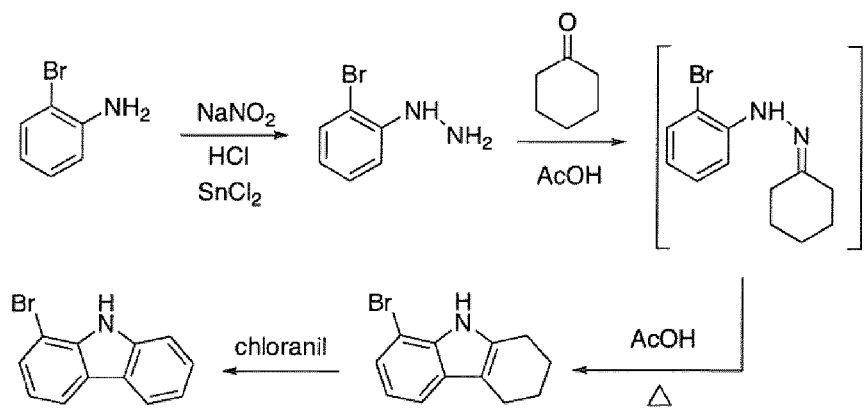
FIG. 14 is a scheme showing the synthesis of 1-bromo-carbazole.

The unsubstituted carbazole derivative (3$_H$-H) required use of 1-bromo-carbazole which was prepared according to the sequence shown in FIG. 14. 2-bromophenylhydrazine was added to a solution of cyclohexanone in glacial acetic acid to form 2-bromophenylhydrazone, which undergoes cyclization under reflux in the same solution, producing 1,2,3,4-tetrahydrocarbazole. Dehydrogenation of tetrahydrocarbazole is carried out with chloranil in boiling xylene, to give 1-bromo-carbazole (FIG. 14). The dehydrogenation may also be carried out with palladium on charcoal.

Figure 15:
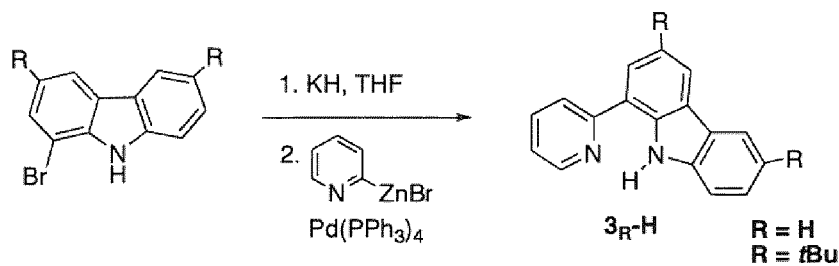
FIG. 15 is a scheme showing the synthesis of $3_{tBu}$-H and $3_H$-H.

These bromo-carbazoles were reacted with 2-pyridylzinc bromide in THF, using tetrakis(triphenylphosphine)palladium(0) as precatalyst, under Negishi coupling conditions the coupling product was formed in 85% yield (FIG. 15). For this coupling reaction it was necessary to protect the nitrogen in the carbazole fragment because of the susceptibility of aryl zinc compounds to protonolysis. This was done simply by deprotonating the carbazole nitrogen with KH and performing the coupling reaction on the potassium salt of the carbazole.

Using examples of the ligands produced as described above, boron difluoride complexes were prepared according to procedures described below.

Figure 16:
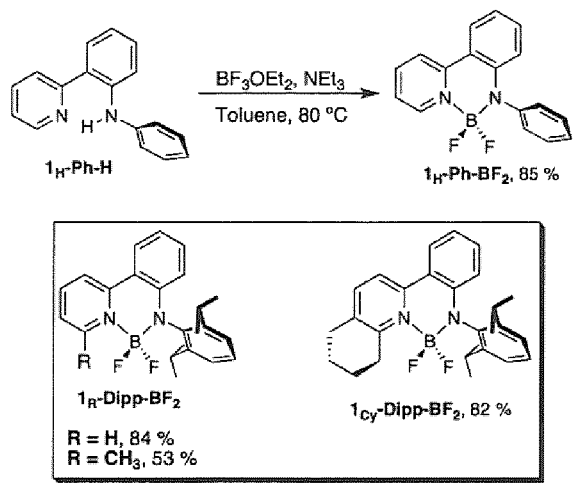
FIG. 16 is a scheme showing the synthesis of $1_H$-Dipp-BF$_2$, $1_{Cy}$-Dipp-BF$_2$, and $1_H$-Ph-BF$_2$.

Synthesis of Boron Difluoride Complexes Supported by 2-(2-pyridyl)-N-arylanilido Ligands For the synthesis of the desired boron difluoride 2-(2-pyridyl)-N-arylanilido compounds an existing route was utilized (FIG. 16). A toluene solution of the proteo ligand and triethylamine was stirred for 10 minutes and boron trifluoride etherate was added dropwise at room temperature. After 5 minutes of addition, the yellow solutions started to change their color to bright green, displaying fluorescence under UV light (254 nm). After stirring for 15 minutes at room temperature, the reaction mixture was heated to 80° C. for one hour. Due to the conjugation present in both the 2-(2-pyridyl)-N-arylanilido compounds and the boron difluoride derivatives, the reaction could be followed easily by thin layer chromatography. After standard work up, the compounds were isolated as bright yellow solids stable under aqueous and oxygen conditions. All the complexes were synthesized in good yields (over 80%), with the exception of $1_{Me}$-Dipp-BF$_2$ (53% yield).

All compounds were fully characterized by multinuclear NMR spectroscopy, elemental analysis and in most cases X-ray crystallography. In the $^1$H NMR spectra, line broadening is seen in the resonance corresponding to the proton attached to C4, likely due to unresolved coupling to F. The methyl group attached to C1 in $1_{Me}$-Dipp-BF$_2$ appears as a triplet in the $^1$H NMR spectra due to coupling with the fluorine atoms attached to boron.

The $^{13}$C{$^1$H} NMR spectra also display some diagnostic features. In all the complexes the carbon adjacent to the nitrogen in the pyridine ring (C1) appears as a triplet due to a three bond coupling with the fluorine atoms.

The compounds were also characterized by $^{11}$B and $^{19}$F NMR spectroscopy. The $^{11}$B{$^1$H} NMR spectrum of every compound showed a broad triplet due to the coupling with the fluorine atoms. The solid-state structures for all the complexes were elucidated by X-ray diffraction. Single crystals were obtained by layering a concentrated dichloromethane solution of each complex in hexanes.

Figure 18:
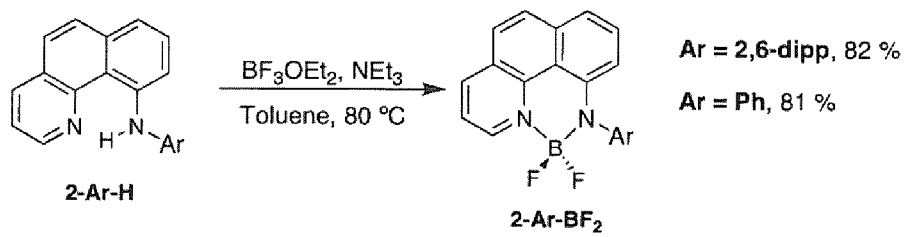
FIG. 18 is a scheme showing the synthesis of 2-Dipp-BF$_2$ and 2-Ph-BF$_2$.

Synthesis of Boron Difluoride Complexes Supported by 10-(N-arylamine)benzo[h]quinolido Ligands The syntheses of 2-Dipp-BF$_2$ and 2-Ph-BF$_2$ were achieved using the same routes as described for the family of boron difluoride 2-(2-pyridyl)-N-arylanilido complexes, except that the reaction was heated to 80° C. for four hours to drive it to completion (FIG. 18). The initial yellow solution turned orange a few minutes after the addition of boron trifluoride etherate and displayed fluorescence upon irradiation with UV light (254 nm). These compounds were purified by flash chromatography on silica gel, giving orange solids.

These Family 2 dyes were also fully characterized by multinuclear NMR spectroscopy and X-ray crystallography. $^{11}$B{$^1$H} NMR spectrum confirmed the assumption that 2-Ph-BF$_2$ and 2-Dipp-BF$_2$ displays C$_s$ symmetry in solution, due to the fact that both spectra showed a single resonance coupled with 2 equivalent fluorine atoms. The chemical shifts for these peaks are 2.3 ppm ($^1J_{B-F}$=27.8 Hz) for 2-Ph-BF$_2$ and 2.1 ppm ($^1J_{B-F}$=29.4 Hz) for 2-Dipp-BF$_2$. These chemical shifts are completely in agreement with the 2-(2-pyridyl)-N-arylanilido complexes and previously reported boron difluoride compounds. $^{19}$F{$^1$H} NMR spectrum showed a quartet centered at −129.0 ppm for 2-Ph-BF$_2$ and at −132.9 ppm for 2-Dipp-BF$_2$. Single-crystals suitable for X-ray crystallography on both complexes were grown by layering a dichloromethane solution of the proper compound with hexanes. In both structures the boron atom presents a distorted tetrahedral geometry with F—B—F angles of 109.14(16)° and 108.39(16)° for 2-Ph-BF$_2$ and 2-Dipp-BF$_2$ respectively. The boron atom deviates from C$_3$N$_2$ plane in 2-Ph-BF$_2$ with a distance of 0.452(4) Å, but 2-Dipp-BF$_2$ is much more planar.

Figure 17:
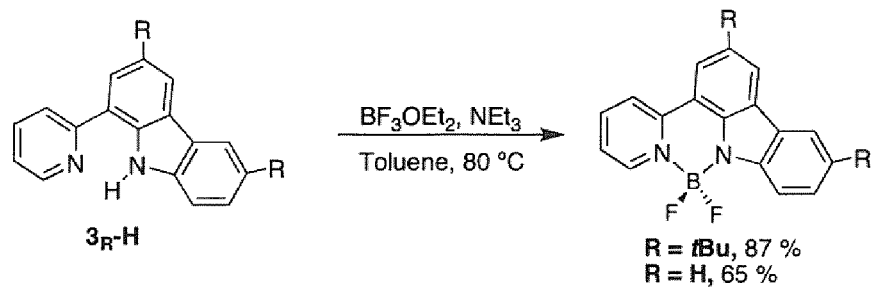
FIG. 17 is a scheme showing the synthesis of $3_{tBu}$-BF$_2$ and $3_H$-BF$_2$.

Synthesis of Boron Difluoride Complexes Supported by 1-(2-pyridyl)-9H-carbazolido Ligands The synthesis of $3_{tBu}$-BF$_2$ and $3_H$-BF$_2$ was achieved using the same protocol utilized to prepare the 10-(N-arylamine)benzo[h]quinolido complexes (FIG. 17).

The proton NMR spectrum of $3_{tBu}$-BF$_2$, shows the characteristic singlets for inequivalent tert-butyl groups at 1.54 and 1.48 ppm. The proton resonance of the hydrogen attached to the C—H carbon closest to nitrogen in the pyridine ring appears as a broad doublet, while its carbon appears as a triplet at 143.4 ppm due to a three bond coupling with fluorine ($^3J_{C-F}$=2.1 Hz) in the $^{13}$C{$^1$H} NMR spectrum. $^{19}$F{$^1$H} and $^{11}$B{$^1$H} NMR spectra are consistent with a complex with C$_s$ symmetry where the two fluorine atoms are equivalent. $^{11}$B{$^1$H} NMR spectrum displays a triplet at 2.46 ppm with a fluorine coupling of 28.2 Hz and $^{19}$F{$^1$H} NMR spectrum shows a broad quartet at −135.3 ppm.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

The invention claimed is:
1. A fluorophore shown by formula (1), or a salt thereof,

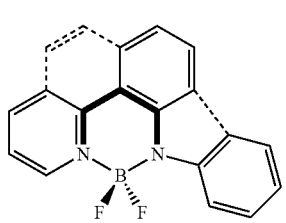

(1)

wherein bonds indicated by dotted lines may be independently present or absent; and each hydrogen atom may be independently substituted by an alkyl group.

2. The fluorophore of claim 1, wherein at least one said hydrogen is substituted by a said alkyl group.

3. The fluorophore of claim 2, wherein said alkyl group is a linear, branched or cyclic monovalent hydrocarbon radical having up to 20 carbon atoms.

4. The fluorophore of claim 1, wherein said fluorophore has a Stokes shift of about 70 nm to about 140 nm.

5. The fluorophore of claim 1, wherein said alkyl group is a linear, branched or cyclic monovalent hydrocarbon radical having up to 20 carbon atoms.

6. A fluorophore shown by formula (2), or a salt thereof,

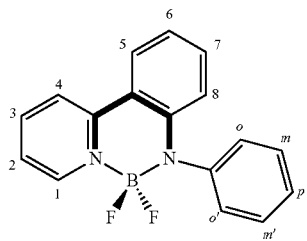

(2)

wherein each hydrogen atom may be independently substituted by an alkyl group.

7. The fluorophore of claim 6, wherein at least one said hydrogen is substituted by a said alkyl group.

8. The fluorophore of claim 7, wherein the hydrogen atoms at positions o and o' are substituted by isopropyl.

9. The fluorophore of claim 8 wherein said fluorophore has a Stokes shift of about 90 nm to about 100 nm.

10. The fluorophore of claim 7, wherein said alkyl group is a linear, branched or cyclic monovalent hydrocarbon radical having up to 20 carbon atoms.

11. The fluorophore of claim 6, wherein said alkyl group is a linear, branched or cyclic monovalent hydrocarbon radical having up to 20 carbon atoms.

12. A fluorophore shown by formula (2), or a salt thereof,

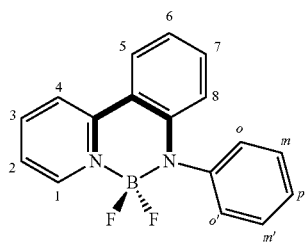

(2)

wherein the hydrogen atoms at positions 1 and 2 are substituted by a —(CH$_2$)$_4$— group such that said group bridges positions 1 and 2, and wherein the hydrogen atoms at positions o and o' are substituted by isopropyl.

13. The fluorophore of claim 12 wherein said fluorophore has a Stokes shift of about 95 nm to about 105 nm.

14. A fluorophore shown by formula (3), or a salt thereof,

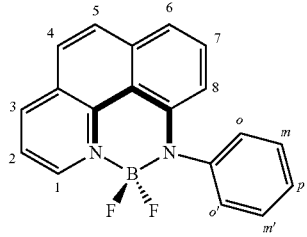

(3)

wherein each hydrogen atom may be independently substituted by an alkyl group.

15. The fluorophore of claim 14, wherein at least one said hydrogen is substituted by a said alkyl group.

16. The fluorophore of claim 15, wherein said alkyl group is a linear, branched or cyclic monovalent hydrocarbon radical having up to 20 carbon atoms.

17. The fluorophore of claim 14 wherein the hydrogen atoms at o and o' are substituted by isopropyl.

18. The fluorophore of claim 17 wherein said fluorophore has a Stokes shift of about 98 nm to about 108 nm.

19. The fluorophore of claim 14 wherein said fluorophore has a Stokes shift of about 114 nm to about 124 nm.

20. The fluorophore of claim 14, wherein said alkyl group is a linear, branched or cyclic monovalent hydrocarbon radical having up to 20 carbon atoms.

21. A fluorophore shown by formula (4), or a salt thereof,

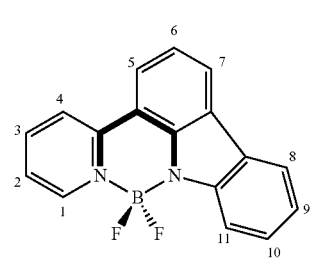

(4)

wherein each hydrogen atom may be independently substituted by an alkyl group.

22. The fluorophore of claim 21, wherein at least one said hydrogen is substituted by a said alkyl group.

23. The fluorophore of claim 22, wherein said alkyl group is a linear, branched or cyclic monovalent hydrocarbon radical having up to 20 carbon atoms.

24. The fluorophore of claim 21 wherein the hydrogen atoms at positions 6 and 9 are substituted by tert-butyl.

25. The fluorophore of claim 21, wherein said alkyl group is a linear, branched or cyclic monovalent hydrocarbon radical having up to 20 carbon atoms.

26. A method of producing a fluorophore shown by formula (1), said method comprising the steps of:
providing a ligand capable of chelating to a BF$_2$ center,
mixing said ligand with a solution of triethyl amine, and
adding boron trifluoride etherate to said solution,
wherein formula (1) is as follows:

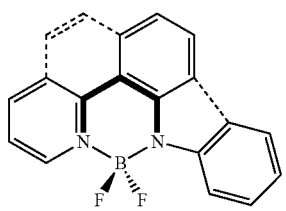

(1)

wherein bonds indicated by dotted lines may be independently present or absent; and each hydrogen atom may be independently substituted by an alkyl group.

* * * * *